United States Patent [19]
Wilkerson

[11] Patent Number: 5,623,204
[45] Date of Patent: Apr. 22, 1997

[54] EDDY CURRENT PROBE

[76] Inventor: Brian Wilkerson, 14837 - 72nd Pl. NE., Bothell, Wash. 98011

[21] Appl. No.: 442,332

[22] Filed: May 16, 1995

Related U.S. Application Data

[63] Continuation-in-part of Ser. No. 62,589, May 17, 1993, abandoned.

[51] Int. Cl.⁶ .................. G01N 27/90; H01H 85/165
[52] U.S. Cl. ............................. 324/228; 336/228
[58] Field of Search ................... 324/228, 237, 324/238, 219, 220, 221, 234, 239, 240, 241, 242, 243, 225, 236, 207.16, 207.15, 207.19; 336/221, 228, 225

[56] References Cited

U.S. PATENT DOCUMENTS

| | | | |
|---|---|---|---|
| 543,843 | 8/1895 | Biggar | 324/228 |
| 2,753,532 | 7/1956 | Ashby et al. | 336/221 |
| 2,779,916 | 1/1957 | Poole | 324/225 |
| 3,020,527 | 2/1962 | MacLaren | 336/221 |
| 3,052,837 | 9/1962 | Arbogast et al. | 324/225 |
| 4,088,953 | 5/1978 | Sarian | 324/238 |
| 4,134,067 | 1/1979 | Woodbury | 324/219 |
| 4,659,990 | 4/1987 | Torre | 324/238 |
| 4,855,677 | 8/1989 | Clark, Jr. et al. | 324/220 |
| 4,952,875 | 8/1990 | Adams et al. | 324/220 |

*Primary Examiner*—Sandra L. O'Shea
*Assistant Examiner*—Roger Phillips
*Attorney, Agent, or Firm*—David L. Tingey

[57] ABSTRACT

An eddy current probe having an increased depth penetration. The probe includes an eddy current test assembly formed in the outer surface of a shoe that rotates within a tubular test specimen. The eddy current test assembly includes a pair of differentially-connected electromagnetic coils whose axes are parallel and lie in a plane perpendicular to the direction of the axis of the tubular test specimen. The probe assembly further includes a magnetically permeable backing plate that is closely adjacent to the innermost ends of the two differentially-connected coils. The differentially-connected coils are driven with a signal having a predominant frequency that is less than the natural resonant frequency of the eddy current probe. Flaws and other non-uniformities in the tubular test specimen are detected as the differentially-connected coils travel pass the location of the flaw. The presence of the backing plate increases the depth of penetration of the magnetic fields produced by the differentially-connected coils into the tubular test specimen, and driving the coils with a frequency that is less than their natural resonant frequency causes the depth of penetration to be further increased.

21 Claims, 7 Drawing Sheets

EDDY CURRENT PROBE

This is a continuation-in-part of Ser. No. 08/062,589 filed in the United States May 17, 1993 now abandoned.

TECHNICAL FIELD

The invention pertains generally to non-destructive testing (NDT) probes for inspecting for structural anomalies in alloys, and more particularly, to an NDT probe utilizing differentially wound coils of matched inductance driven by an alternating voltage source in the frequency range of 1,000 Hz to 25,000 Hz to generate eddy currents that permit improved inspection at greater depths.

BACKGROUND

Using eddy current probes for non-destructive testing of various alloys is common in a variety of environments. The testing applications include alloy sorting, detecting cracks in airframes and remotely testing structures in hazardous environments, such as nuclear power plant heat exchanger tubing. Such testing applications are frequently essential for quality control and prevention of potentially catastrophic failures of structural members, weldments and other types of joints.

It is desirable to test for structural flaws as deeply as possible for several reasons. One reason is that the access to a potentially flawed location in a test specimen may be limited to a region that is significantly displaced from the potential flaw location. Another is that it is desirable to detect a propagating flaw long before it reaches a critical size or comes close to breaching a barrier such as the barrier between radioactive and non-radioactive water in a nuclear power plant.

An additional consideration in the nuclear power plant application is that eddy current test probes must be relatively small. Typically, an eddy current test probe is inserted in a steam tube past the locations where any flaws are expected and then rotated circumferentially as the eddy current test probe is withdrawn from the steam tube. Therefore, the interior diameters of the steam tubes in a nuclear steam generator limit the physical size of an eddy current test probe and, consequently, the size of the coils in the eddy current test probes. This size limitation, in turn, places restrictions on the physical configuration of a probe and on electrical parameters of the eddy current test coils, and affects the depth penetration of the eddy currents the eddy current test coils generate, as will be discussed below.

Accordingly, it is an objective of the present invention to provide an eddy current test probe with enhanced test depth performance.

It is a further objective of the present invention to provide an eddy current test probe with enhanced test depth performance in space-limited applications such as inside tubulartest specimens.

It is a still further objective of the present invention to provide a test coil assembly with enhanced sensitivity to flaws in test specimens.

SUMMARY OF THE INVENTION

An eddy current probe for testing tubular test specimens includes a probe means and a differential test coil means. The probe means supports the differential test coil means during testing, and the differential test coil means is optimized to operate at a driving frequency in the range of 1 kHz to 25 kHz. The differential test coil means includes a pair of matched inductance coils and a backing plate mounted to the coils whereby the backing plate serves to increase the inductance of the coils without increasing the coils' resistance. In one preferred embodiment, the test coil assembly comprises two axial coils and a magnetically permeable backing member. Each axial coil has two ends, and the two axial coils are held together so that their axes are substantially parallel and one end of each coil substantially terminates in the same plane transverse to the axes. The magnetically permeable backing member is mounted adjacent to both of the substantially coterminal ends of the two axial coils.

The test coil assembly can be configured for use in tubular test specimens having a 0.475 inch inner diameter (ID) and is generally of cylindrical shape with a pair of spring biased radially disposed shoes, one shoe having embedded in it adifferential test coil assembly. The test coil assembly includes a pair of axially parallel coils bonded to each other and a disk-shaped back plate mounted to an axial end of the bonded coils. Each coil is formed of windings about #77 ferrite cores which have a D-shaped cross-section. The preferred embodiment is optimized to operate efficiently with a driving frequency of about 5 kHz. In another embodiment, the invention is an eddy current probe for non-destructive testing of alloys. The eddy current probe comprises an eddy current transducer including an eddy current probe and a differential test coil. The eddy current probe supports the differential test coil during testing of the alloys. The differential test coil includes at least two coils and a backing plate. The coils are juxtaposed in near contact, have matched inductances and are mounted to the backing plate at ends of the coils.

In still another embodiment, the invention is an eddy current probe for non-destructive testing of alloys. The eddycurrent probe comprises a probe housing, a test coil member and an inductance enhancing member. The test coil member is mounted in the probe housing to generate eddy currents in a test specimen of one of the alloys to be tested. The eddy currents are generated by excitation by an alternating current. The inductance enhancing member is disposed proximate the test coil member in the probe housing and has a permeability selected so that the depth of penetration of the test eddy currents is optimized for the alloys to be tested when the operating frequency of the alternating current is substantially in therange of 1 kHz to 25 kHz.

To provide a complete disclosure of the invention, reference is made to the appended drawings and following description of one particular and preferred embodiment of the invention.

BRIEF DESCRIPTION OF THE DRAWINGS

FIG. 3c is a top view of the test coil assembly of FIG. 3a.

DETAILED DESCRIPTION OF THE PREFERRED EMBODIMENT

Figure 1:
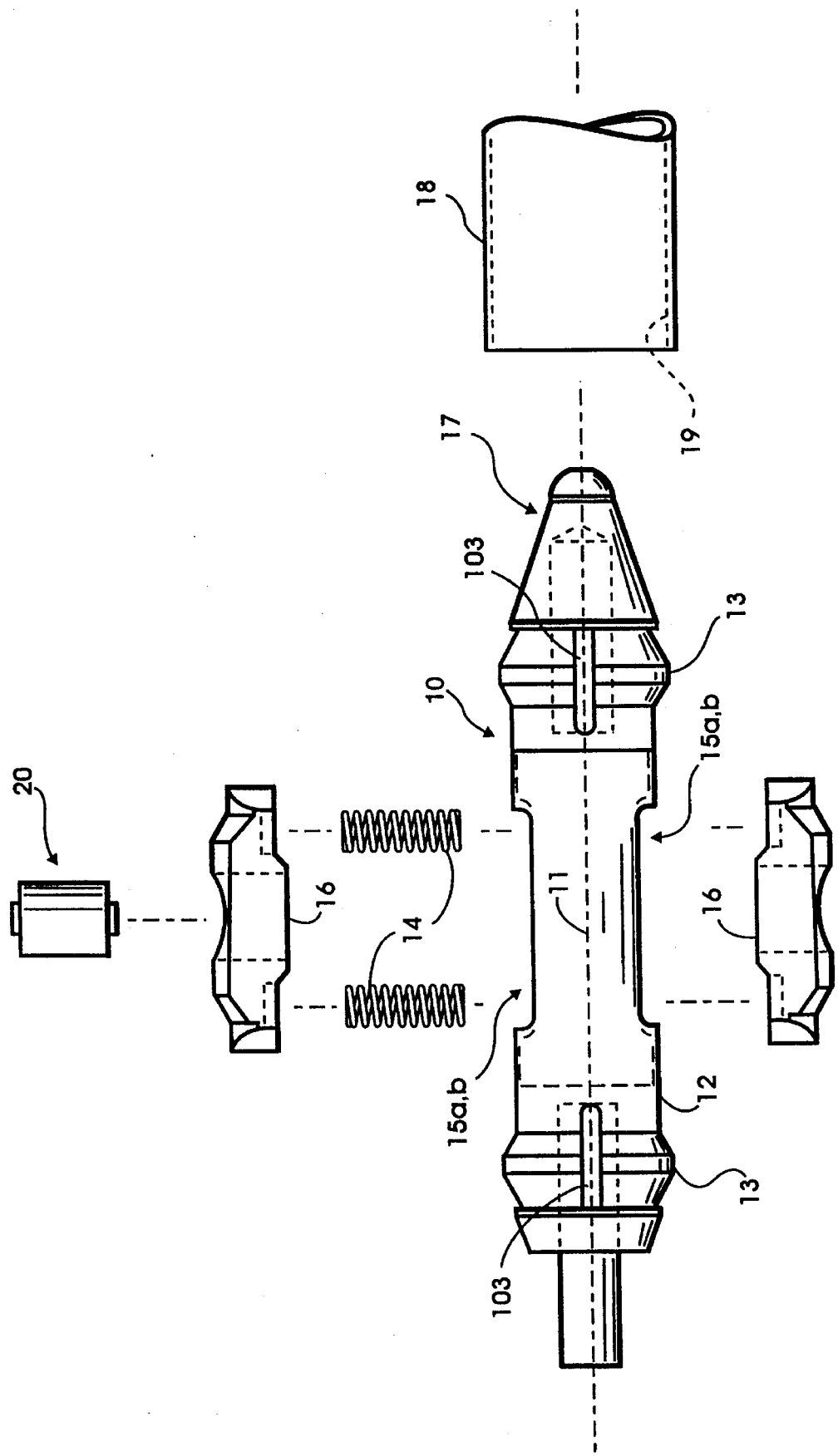
FIG. 1 is a partially exploded side elevation view of aneddy current probe incorporating the present invention.
Figure 2:
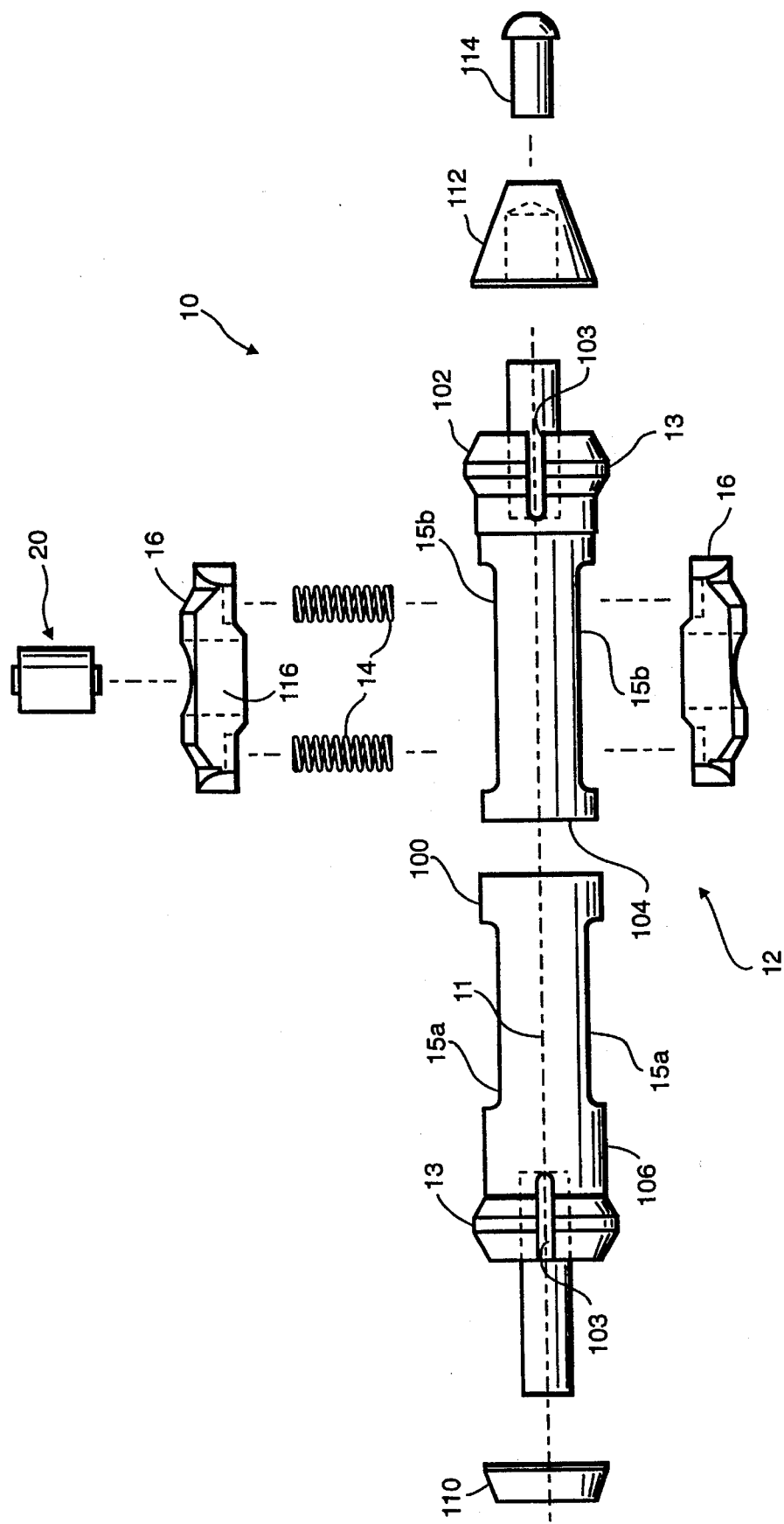
FIG. 2 is a fully exploded side elevation view of the eddy current probe of FIG. 1.

FIG. 1 is a partially exploded side elevation view of an eddy current probe incorporating the present invention and FIG. 2 is a fully exploded side elevation view of the eddy current probe of FIG. 1. FIGS. 1 and 2 show an eddy current probe assembly 10 incorporating the invention. The eddy current probe assembly 10 has a probe body 12 which is generally cylindrical in shape with larger diameter centering feet 13 at each end. The eddy current probe assembly 10 is radially symmetric with respect to an axis 11. The centering feet 13 are sized to permit the probe assembly 10 to be slid into a tubular test specimen 18. One end of the probe assembly 10 has a generally conically-shaped nose 17 to assist in inserting the probe assembly 10 into the tubular test specimen 18. The probe assembly 10 further includes biasing springs 14 and shoes 16 which are normally nested in radially opposed cavities 15.

A test coil assembly 20 is embedded in one of the shoes 16 The biasing springs 14 urge the shoes 16 radially outward from probe body 12 thereby bringing shoes 16 and test coil assembly 20 in contact with the inner wall 19 of the tubular test specimen 18. The test coil assembly 20 is recessed approximately 0.010" into the one shoe 16, so that the test coil assembly 20 is spaced away from the inner wall 19 of the tubular test specimen 18.

The eddy current probe assembly 10 is typically used to test weldments and the metallurgical integrity of tubing associated generators and other applications having hard-to-reach locations or hazardous environments which require remote testing. A commonly tested weldment that can be tested by an eddy current probe assembly 10 is found where the steam tubes in a nuclear steam generator are welded to a tube sheet with in a steam generator. To test the weldment of a particular steam tube to the tubesheet, the eddy current probe assembly 10 is attached to a conventional cable and a conventional positioning means (not shown) which controls the translation and rotation of the eddy current probe assembly 10 within the steam tube (exemplified by the tubular test specimen 18). The cable electrically connects the eddy current probe assembly 10 to an electronics package 19 which has an alternating current (AC) signal generator (not shown) that provides AC electrical power to the test coil assembly 20 in the eddy current probe assembly 10. The electronics package also processes signals representing perturbations in the tubular test specimen 18 that are detected by the eddy current probe assembly 10 and produces an output signal representing the processed data in a variety of ways. The output signal can be in the form of, e.g., audio signals or Lissajous figures, or can be used to produce strip charts and data listings.

FIG. 2 is a fully exploded side elevation view of the eddy current probe assembly 10 of FIG. 1. The largest components of the eddy current probe assembly 10 are the first cylindrical body 100 and the second cylindrical body 102.

Both the first and second cylindrical bodies 100 and 102 are thin cylindrical shells that are concentric with the axis 11 after they are assembled to form the eddy current probe assembly 10. The centering feet 13, formed on both the first and second cylindrical bodies 100 and 102, are cut with slots 103 so that the shoulders will exhibit springiness that will allow the eddy current probe assembly 10 to center itself as it passes through the tubular test specimen 18. The inner diameter of the first cylindrical body 100 is larger than the outer diameter of the second cylindrical body 102. This allows the second cylindrical body 102 to slide into the first cylindrical body 100 until the inner end 104 of the second cylindrical body 102 abuts against an inner surface 106 formed within the first cylindrical body 100. The cavities 15a, formed in the first cylindrical body 100, are smaller than the cavities 15b, formed in the second cylindrical body 102, but they are generally aligned after the first and second cylindrical bodies 100 and 102 are assembled, as shown in FIG. 1. The axial extent of the shoes 16 is greater than the axial extent of the cavities 15a, but less than the axial extent of the cavities 15b. This allows the shoes 16 to first be assembled, with the springs 14, in the second cylindrical body 102, where they are compressed as the first cylindrical body 100 is slid over the second cylindrical body 102 until the cavities 15a and 15b align. This will capture the shoes 16 within the assembled first and second cylindrical bodies 100 and 102. Each of the shoes 16 are shaped so that they extend sufficiently in a radial direction until their most radially distant portions ride against the inner surface 19 of the tubular test specimen 18. The eddy current test assembly 10 also includes the two first and second frustoconical nose pieces 110 and 112, which fit over cylindrical extensions on the first and second cylindrical bodies 100 and 102, respectively. The second nose piece 112 is held against the cylindrical projection of the second cylindrical body 102 by the screw 114. The cable used to drive the eddy current test assembly 10 into the test specimen 18 is attached to the cylindrical projection of the first cylindrical body 100 in a conventional manner. All of the components of the eddy current test assembly 10 described so far, except for the springs 14, the screw 114 and the shoes 16 are conveniently made from natural nylon, which may be conveniently cast and machined as necessary. The shoes 16 are made from a material such as the plastic sold under the trademark TORLON, which is owned by AMOCO Chemical Corporation. At least one of the shoes 16 has a radially-extending cavity 116 formed torrent test coil assembly 20. The cross-section of the radially extending cavity 116 is roughly circular.

Figure 3A:
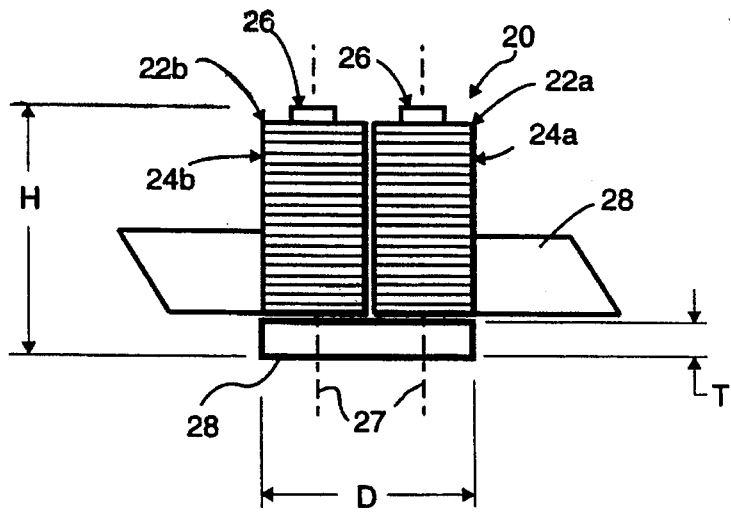
FIG. 3a is side view of an eddy current test coil assembly of the present invention.

FIG. 3a is side view of an eddy current test coil assembly of the present invention. The test coil assembly 20 comprises two electrical coils 22a and 22b. The coils 22a and 22b are connected physically in juxtaposition and electrically to produce magnetic fields that oppose each other. The coils are electrically driven to generate a magnetic field intended to penetrate a test article brought in proximity to the coils. Test article material properties effect changes in the fields which are detected as voltage changes in each of the coils. Differentiating the voltages in each coil removes detected features common to each coil.

Each coil 22 includes a winding 24 and an elongated ferritic core 26 on each coil axis. Multiple winds are employed around the core longitudinal on the coil axes, respectively, to increase field strength and coil inductance. Each core necessarily terminates substantially at a coil first end so that test article can be passed in close proximity to the coil ends. Fields generated by the coils and enhanced by the cores then project from the coil axes and cores out and away from the coil ends, penetrating into the test article. With no permeable material external to the circumference of the coils, the fields intentionally diverge from the coil first ends to penetrate the test article with low frequency, thereby increasing penetration.

In a preferred embodiment of the coil assembly 20, each core 26 has a D-shaped (semi-circular) cross-section with an axis 27, the winding 24 being wound tightly around the core 26. The wire in the winding 24 is approximately 0.003 inch in diameter. This gives each of the coils 22 a rounded D shape. A first end of each of the cores 26 extends beyond the winding 24 by a distance that is approximately equal to the thickness of one wire. The other (second) end of each of the cores 26 also extends slightly beyond the winding 24, generally by a distance that is greater than the thickness of one wire yet terminating substantially at the coil first ends. After the winding 24 is formed around each of the cores 26, the flattened portions of the two coils 22 are attached to each other in near contact with the coil axes 27 parallel, to form the test coil assembly 20. With the coils necessarily in near contact, side-by-side, they are thus suited as cooperating differential coils closely aligned such that normal test article local features are removed during coil signal differentiation leaving only test article material flaws detected by one coil but not by the other as the coils are passed over the test article.

The two first ends of the two cores 26 are placed close together at one end of the test coil assembly 20 so that they lie in roughly the same plane 28. A backing plate 28, which is a circular disk, is attached, by means of epoxy, to the first ends of each of the two cores 26 such that the plate fully covers the ends of the coils to form the test coil assembly 20. The effect of the backing plate is incorporated in the coil core constant, K, as given in the equation for coil inductance given below. It is well known that the core constant will vary with the material and physical properties of the core material. That is, a backing plate with high mass will increase the core constant as will a material with high permeability. In a preferred embodiment of the coil assembly 20, the backing plate 28 is fabricated from a material having a permeability of substantially 500 or greater, such as HY-MU-80m, and configured thin to accommodate the physical size limitation of the small probe, but extending to the outer envelope of the coils to derive maximum benefit of the largest possible plate within geometric constraints of the probe.

The test coil assembly 20 has a roughly circular cross-section that fits into one of the circular cavities 116 formed in the shoes 16. The reason that the test coil assembly 20 is embedded in one of the shoes 16 (see FIG. 1) is so that wearing forces will be distributed over a larger surface area than that of the test coil cores 26. These forces are associated with repeated passage of the eddy current probe assembly 10 through tubing, exemplified by the tubular test specimen 18. The test coil assembly 20 is placed in the cavity 116 and held in place with an epoxy.

In an exemplary preferred embodiment of the eddy current probe assembly 10 for optimal use in tubes having an inner diameter of 0.475 inch, the backing plate 28 has a thickness (T) of 0.050 inch and a diameter (D) of 0.245 inch. The overall height (H) of coil assembly 20 is 0.175 inch.

Figure 3B:
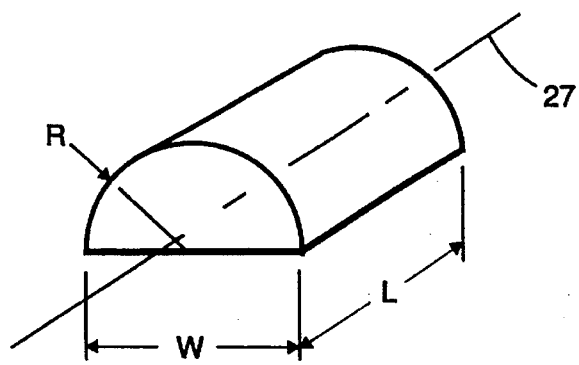
FIG. 3b is an isometric view of a split core for a test coil of the present invention.
Figure 3C:
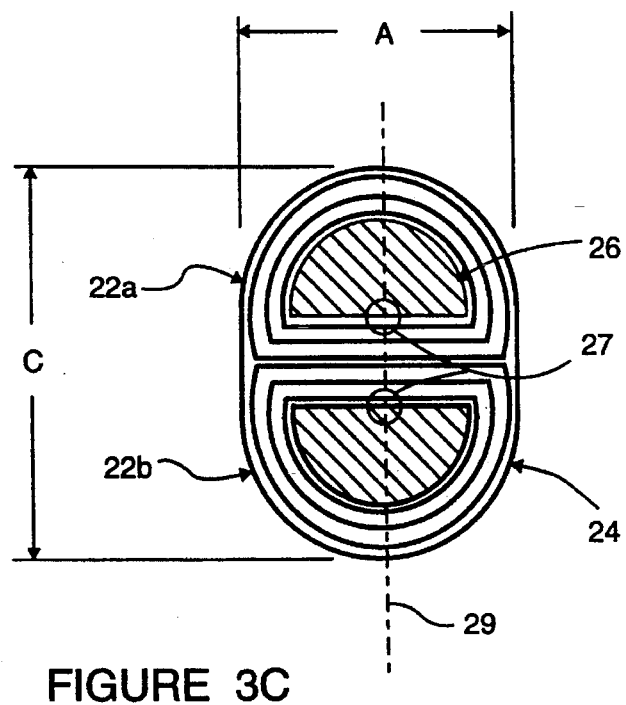

FIG. 3b is an isometric view of a core 26 for a test coil of the present invention. Each of the cores 26 in the exemplary preferred embodiment has a length (L) of 0.125 inch, a width (W) of 0.130 inch and a radius (R) of 0.065 inch. The cores 26 can be made from #77 ferrite, which has a permeability of 2000. FIG. 3c is a top view of the test coil assembly of FIG. 3a. It shows the coils 22a and 22b bonded together. The circumferential dimension (C) of the preferred embodiment of the bonded coils is 0.240 inch and the axial dimension (A) of the bonded coils is 0.180 inch.

The test coil assembly 20 is also known as a self comparison differential test coil because the coils 22a and 22b are electrically connected to produce magnetic fields that oppose each other. Accordingly, if both of the coils 22a and 22b are represented with identical test specimens (or identical portions of the same test specimen), the output of one coil 22a will cancel the output of the other coil 22b. Perturbations or disturbances (flaws) in the different portions of the test specimen create changes in the eddy currents due to changes in the electrical properties of the material. The changes in the eddy currents will produce changes in their associated equilibrium fields. These changes affect the primary fields of the coils and result in a variance of the impedance of the test coil assembly 20. The difference in the impedances of the two coils 22a and 22b is typically measured by using a conventional bridge circuit and is then displayed and evaluated. The existence of the perturbations in the test specimen can be emphasized by scanning the test coil assembly 20 past the area where the perturbations occur in the tubular test specimen 18.

The axes 27 of the two coils 22a and 22b in the test coil assembly 20 are preferably placed in the plane 29 containing the direction in which the tubular test specimen 18 is scanned Therefore, since it is easiest to rotate the probe assembly 10 at a substantially fixed rate (say, 60 revolutions per minute), the axes 27 of the two coils 22a and 22b lie in a plane 29 that is perpendicular to the axis 11 of the tubular test specimen 18.

Figure 4:
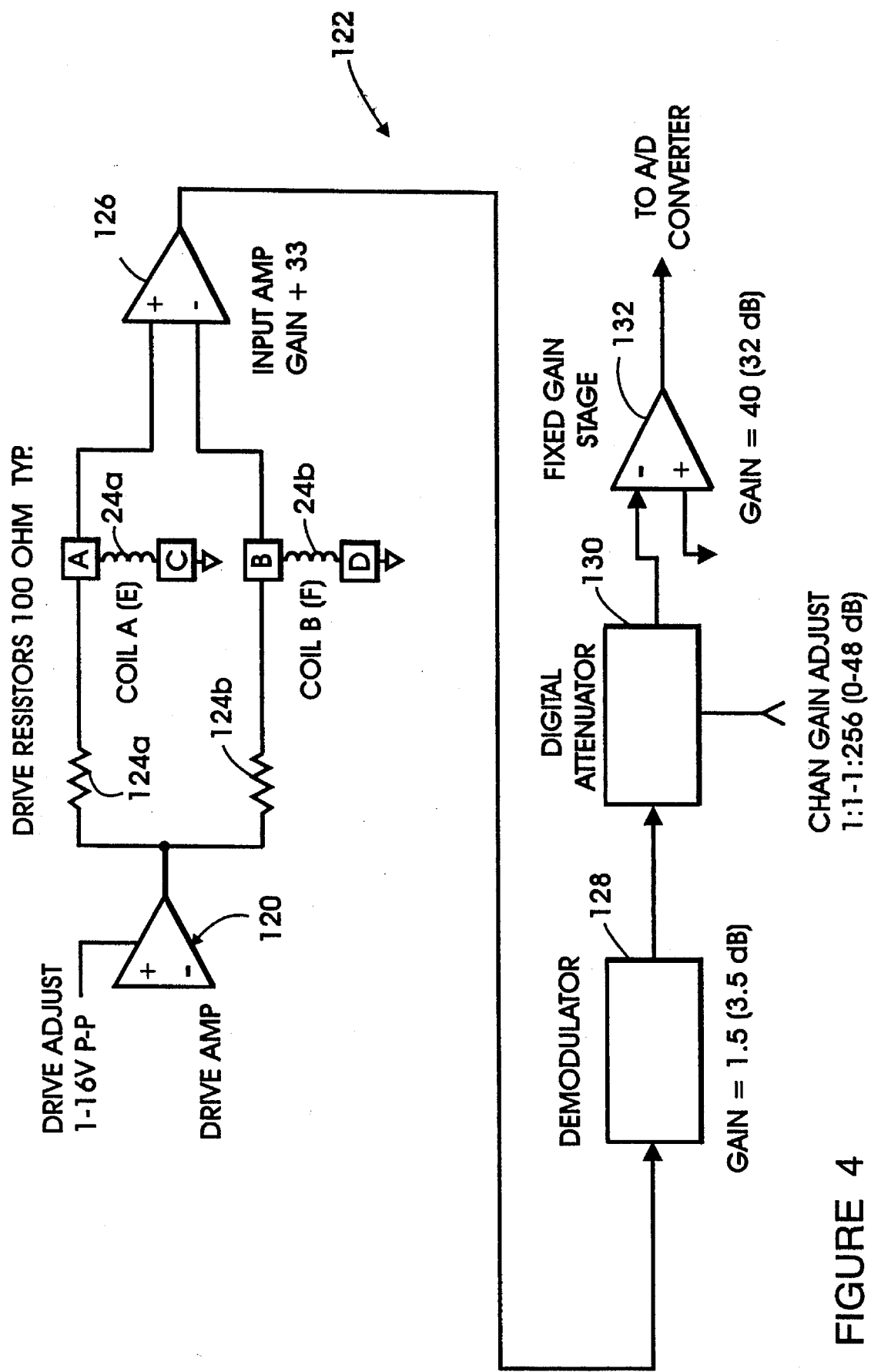
FIG. 4 is a block diagram of electronic circuitry fordriving and processing signals from the eddy current probe shown in FIGS. 1–3.
Figure 5:
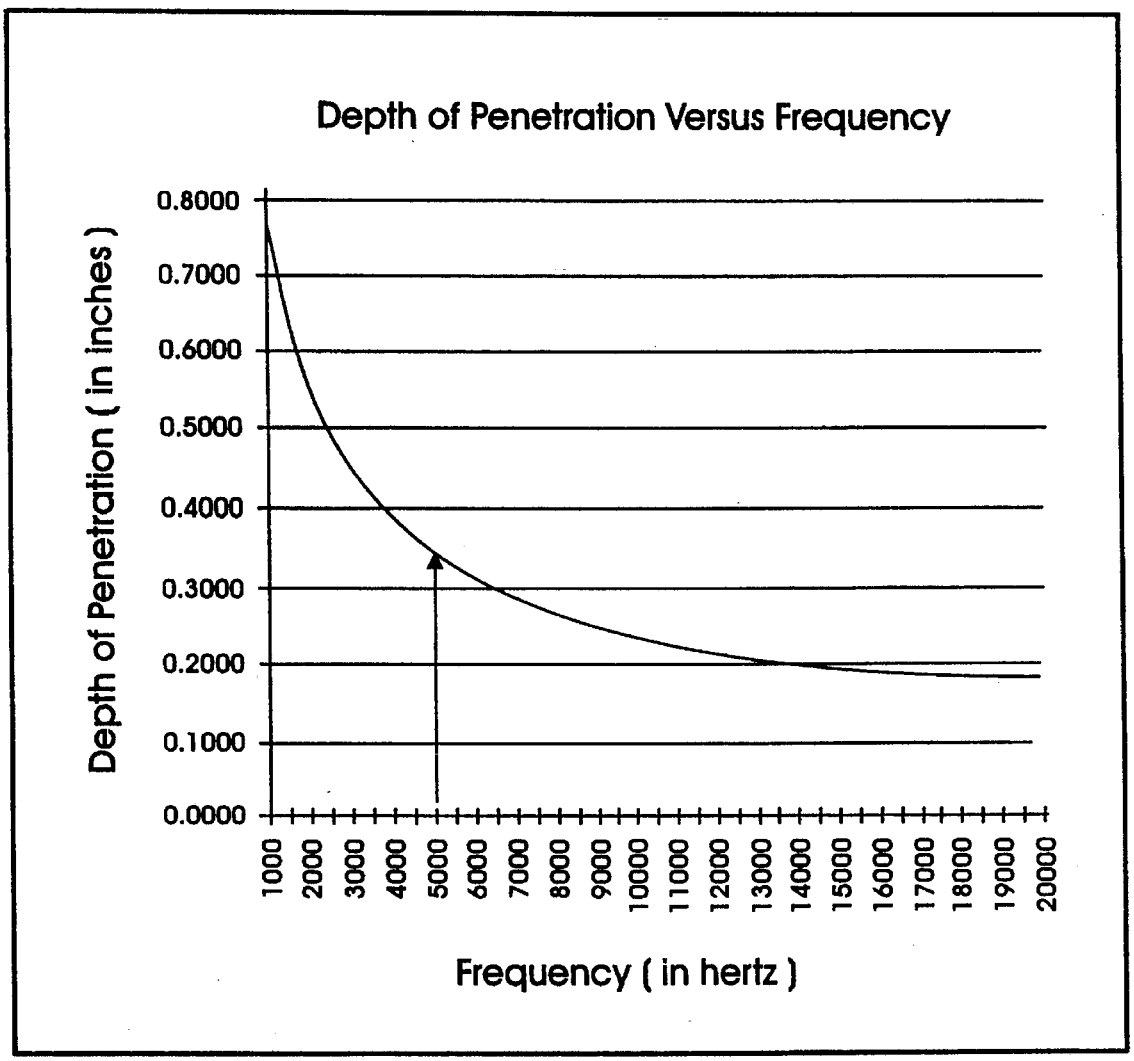
FIG. 5 is a graphical representation of eddy current depth penetration versus test coil operating frequency.

FIG. 4 is a block diagram of electronic circuitry for driving and processing signals from the eddy current probe shown in FIGS. 1–3. The electronic circuitry includes an adjustable drive amplifier 120 for producing an AC drive signal at a desired frequency. It also includes the electrical circuitry of the eddy current probe itself and output circuitry 122 for processing the signals produced by the eddy current probe. The electrical circuitry of the eddy current probe includes the inductances of each of the two coil windings 24a and 24b and the respective resistances 124a and 124b associated with each of the two coil windings 24a and 24b. The output circuitry 122 includes a differential amplifier 126, a demodulator 128, a digital attenuator 130, and a fixed gain stage amplifier 130. In operation, the adjustable drive amplifier 120 produces the AC drive signal at the desired frequency. The AC drive signal drives each of the two parallel electrical circuits including the series resistances 124 and the shunt inductances 24. The self-inductances of the two regions of the material being measured affect the inductances of the two coil windings, as described above and cause the output signals that are sent to the differential amplifier 126 to change depending upon the magnetic properties of the two regions of the material being measured. If the two regions of the materials are the same, the output signals will be the same and the output of the differential amplifier 126 will be zero. If, however, the two regions of the material being measured are different (for example, if one of the regions contains a flaw which the other region does not contain), the amplitudes and phases of the two output signals will be different and their difference will also be different. The signal produced by the differential amplifier 126 is the sum of two sinusoidal signals at the desired frequency. This signal can be demodulated by the demodulator 128 to produce a low frequency analog signal. The low frequency analog signal is then attenuated by the digital attenuator 130 (in accordance with the adjustment 134) to produce the signal that is amplified by the fixed gain stage amplifier 132. The analog signal produced by the fixed gain stage amplifier 132 can then be digitized by a conventional analog-to-digital (A/D) converter (not shown) for display and/or recording. Enhanced eddy current test depth performance is directly related to the operational frequency of the test coil assembly 20. A plot of this relationship is shown in FIG. 5, which is a a graphical representation of eddy current depth penetration versus test coil operating frequency. The formula for standard depth of penetration (the depth in a test specimen where the magnitude of eddy current flow is equal to 37% of the eddy current at the surface of the test specimen) is as follows:

$$\delta = k \sqrt{\rho/(F \times \mu_{rel})}$$

where:

$\delta$=Standard depth of penetration
$\rho$=Resistivity
F=Frequency
$\mu_{rel}$=1 for non-ferromagnetic materials
k=constant (2 for inches, 50 for mm scale)

Using this formula, and assuming k, $\mu_{rel}$ and $\rho$ remain constant, the depth of penetration is inversely proportional to the square root of the frequency, F, at which the coils 22a and 22b are driven.

Empirical studies have shown 5 kHz to be the optimum frequency for flaw detection. To maximize the signal response at 5 kHz the impedance of the electronics package that drives the coils 22a and 22b (nominally 100 ohms) and the combined impedance of the coils 22a and 22b must be matched and the figure of merit, Q, of the test coil assembly 20 must be maximized. It can be seen from the following equation that if the driving impedance is fixed, then the greatest figure of merit, Q, will be obtained when the resistance, R, of the combined test coils 22a and 22b is lowest.

Coil Q=$X_L$/R, where $$X_L = \sqrt{Z^2 - R^2},$$

and Z is the driving impedance (100 $\Omega$).

For example, the figure of merit of a coil 22 with resistance R=1 is, $$Q = \sqrt{(100^2 - 1)} / 1 = 99.995$$

On the other hand, when the resistance R=10, the figure of merit of the coil 22 is, $$Q = \sqrt{100^2 - 10^2} / 10 = 9.9499.$$

This shows that for two coils 22 that are wound to operate at the same frequency (assuming that the coil size and configuration are the same), the one with the lowest resistance will operate more efficiently.

The theoretical test coil inductance, L, needed to operate at 5 kHz is determined by the following formula: where resistance R=1:

$$L = X_L/(2\pi F) \geq L = 99.995/(2\pi \times 5000) = 3.18 \text{ mH}$$

A coil wound about a #77 ferrite core alone, with the geometrical constraints of the preferred embodiment (testing tubes with internal diameters (ID) of 0.475 inch), yields a coil inductance of approximately 0.83 mH when the individual coils 22a and 22b are placed together as a test coil assembly 20. This configuration results in a peak operating frequency of about 20 kHz. To raise the inductance of each of the coils 22a and 22b and thereby reduce the operating frequency of the test coil assembly 20 to 5 kHz, the backing plate 28, made from a material having a permeability of substantially 500 or greater, is mounted to the base of the bonded individual coils 22a and 22b. In the preferred embodiment, HY-MU-80 is chosen for the backing plate 28, but it is recognized that other materials may be substituted for different coil configurations. The addition of the backing plate 28 to the test coil assembly 20 raises the inductance of the coils 22a and 22b to approximately 1.4 mH. With this coil inductance the test coil assembly 20 operates efficiently at 5 kHz even though the center frequency is approximately 11 kHz.

The improved flaw detection performance of the preferred embodiment incorporating a backing plate 28 is illustrated in the FIGS. 6a–7b. The data represented in the Figures was obtained from a model MIZ-40 EDDY CURRENT INSTRUMENT manufactured by Zetec, Inc., 1370 NW Mall St., Issaquah, Wash. In each graph, several traces are shown. Each trace is displaced from the other traces in the "depth" dimension and represents a single circumferential scan of the eddy current probe assembly 10 at a fixed axial position within the tubular test specimen 18. The vertical displacement of a given trace at a given circumferential position indicates the disruption of the magnetic field measured by the test coil assembly 20 and, accordingly, any vertical deviation of the trace indicates the presence of a flaw in the tubular test specimen 18. The leftmost point on each trace corresponds to the same circumferential angle, so that a flaw which causes vertical displacements in several consecutive traces at the same circumferential position represents a linear flaw in the axial direction. Furthermore, the vertical displacement of a trace is an indication of the magnitude of the flaw causing the displacement, so that a large flaw can be distinguished from a small flaw.

Figure 6A:
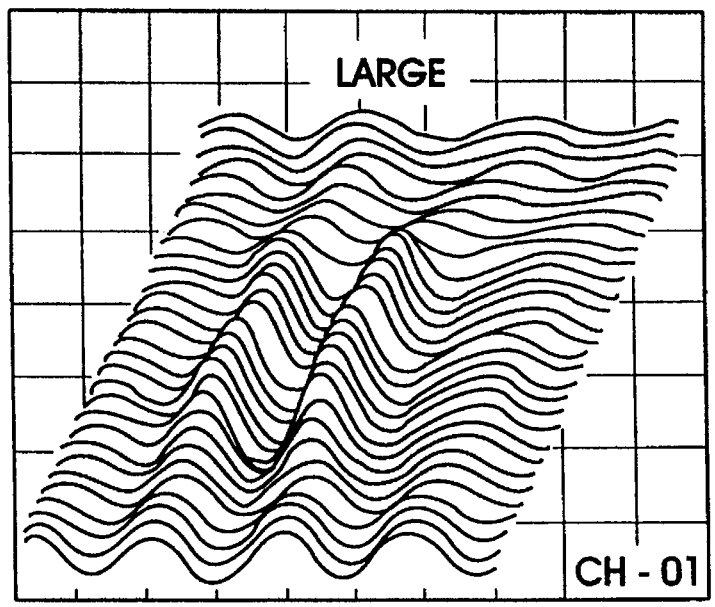
FIG. 6a is a graph of flaw detection data using a probe without the backing plate of the present invention
Figure 6B:
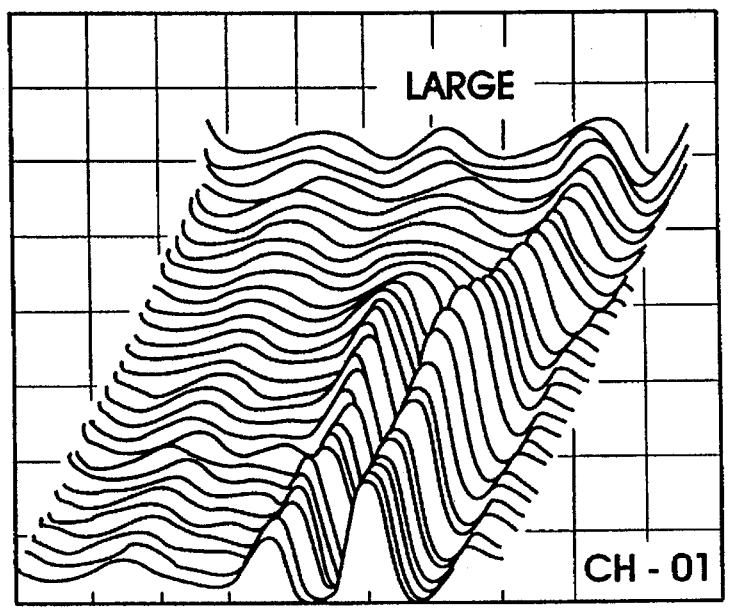
FIG. 6b is a graph of flaw detection data similar to FIG. 6a except the probe used incorporates the backing plate of the present invention.
Figure 7A:
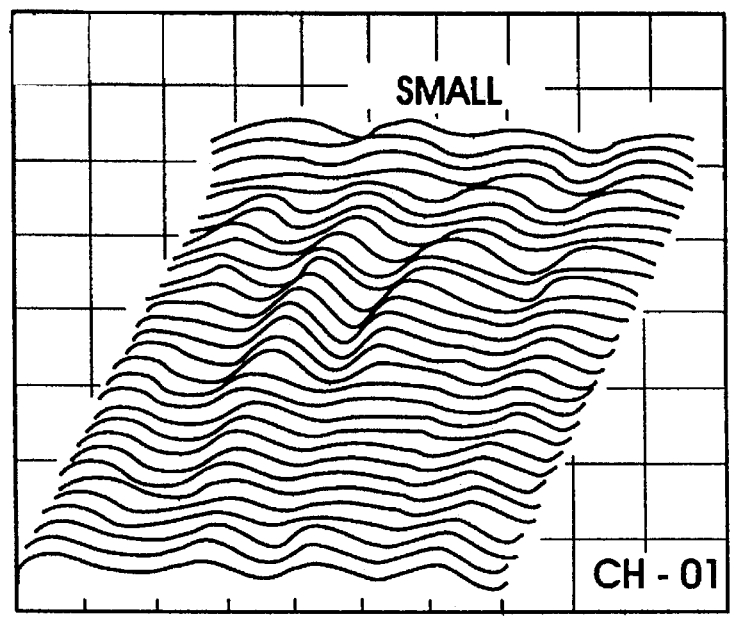
FIGS. 7a and 7b are respectively analogous to FIGS. 7a and 7b except the flaw being detected is of smaller dimensions.
Figure 7B:
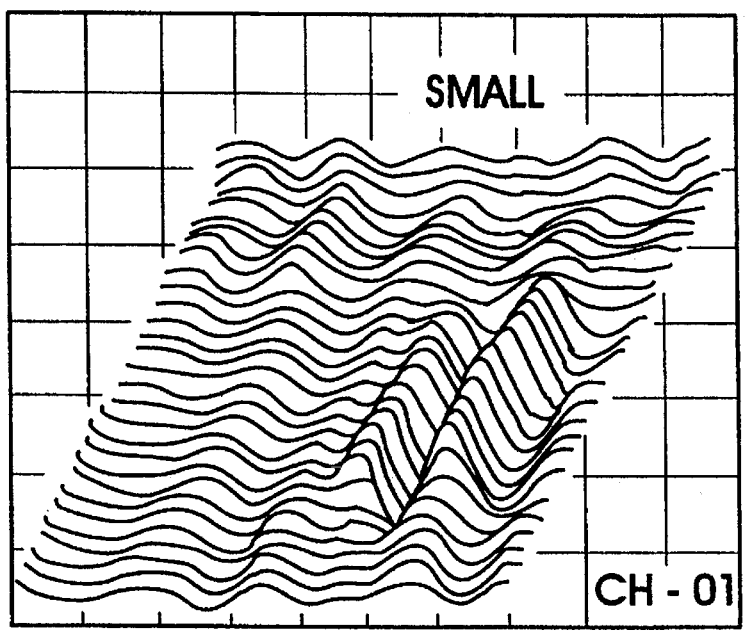

FIG. 6a depicts the result of testing for a "large" defect (0.080" wide×0.080" deep×0.375" long) in a tubular test specimen using a test coil assembly 20 without a backing plate 28. FIG. 6b depicts the results obtained by testing for the same flaw as in FIG. 6a, but using a test coil assembly 20 with a backing plate 28. It can be seen that the test coil assembly 20 detects the presence of the flaw in both cases, but that using a backing plate 28 with the test coil assembly 20 makes the flaw more discernable. Similarly, FIG. 7a depicts the result of testing for a "small" defect (0.040 wide×0.040" deep×0.250" long) with a test coil assembly 20 without a backing plate 28, and FIG. 7b depicts the test result using a test coil assembly 20 with a backing plate 28. Comparison of FIGS. 7a and 7b shows that the use of a backing plate 28 in the test coil assembly 20 enhances the detection of a small flaw, as well.

The inductance, L, of the coils 22a and 22b can also be determined by the following formula:

$$L = R(Nr)2/(6r + 9l + 10b)$$

where:

K=Core constant (0.8 for air core)
N=Total number of turns of wire
r=mean radius of coil
l=length of coil
b=depth of coil L=self inductance The operational environment of the preferred embodiment determines the physical size limitations of the coils 22a and 22b. Accordingly, with the values of r, b and l determined by the environmental limitations, the variables K and N can still be changed. However, to increase N the mean diameter of the wire used must decrease and the wire length must increase to remain within the dimensional limitations. Such changes in wire geometry would necessarily raise the resistance of the coil 22 which will reduce the coil's figure of merit, Q. Hence, the preferred embodiment is designed to raise the core constant, K, without increasing core resistance by incorporating the ferrite cores 26 and the high permeability backing plate 28. While only a particular embodiment has been disclosed herein, it will be readily apparent to persons skilled in the art that numerous modifications can be made thereto, including the use of equivalent means and devices without departing from the spirit of the invention.

We claim:

1. A differential test coil assembly, comprising:

two coil cores with first and second ends, two axial, matched inductance coils, each of which is wrapped around a coil core, each axial coil having first and second ends terminating at respective core first and second ends, the two axial coils being disposed side-by-side with their axes parallel and both first coil and core ends substantially coterminating in a first common plane transverse to the axes so that a test article can be passed in close proximity to coil and core first ends and both second coil and core ends substantially coterminating in a second common plane transverse to the coil axes;

a magnetically permeable backing member attached immediately adjacent to and substantially covering the core and coil coterminal second ends of both axial coils in the second common plane.

2. The test coil assembly of claim 1 in which the backing plate fully covers the coterminal coil ends in near contact therewith.

3. The test coil assembly of claim 1 wherein the backing member has a permeability selected so that the assembly has a low operating frequency of about 5 kHz or lower for enhanced depth of electromagnetic field penetration in a test article.

4. The test coil assembly of claim 1 wherein the coil cores terminate approximately at a second end of each coil such that a test article can be brought into close proximity of the coil second ends.

5. The test coil assembly of claim 1 the test coils further comprise multiple coil winds longitudinal with the coil axes.

6. The test coil assembly of claim 3 wherein the backing member is formed of a material having a permeability of about 500 or greater.

7. The test coil assembly of claim 1 further comprising a core for each coil, each of the cores having a D-shaped cross-section around which a coil is wound, the flat surfaces of the D-shaped cross-sections disposed substantially adjacent and parallel to each other.

8. The test coil assembly of claim 1 wherein the test coil assembly is adapted to be held by a probe assembly that is substantially cylindrical in shape and sized so that the probe assembly can be inserted into a tubular test specimen when it is holding the test coil assembly so that the axes of the two axial coils are substantially transverse to the axis of the tubular test specimen.

9. The test coil assembly of claim 1 wherein the coils are electrically connected in parallel.

10. The test coil assembly of claim 1 in which the coils are electrically driven to generate magnetic fields broadly diverging from the coil axes away from the test coil second ends and returning to the backing member.

11. An eddy current probe for non-destructive testing of alloys, comprising:

an eddy current probe support apparatus and a differential test coil, the eddy current probe support apparatus supporting the differential test coil during testing of said alloy materials, and the differential test coil including at least two axial, matched-inductance coils and a magnetically permeable backing member, the coils being disposed side-by-side with their axes parallel each coil comprising a core with first and second ends around which the coil is wrapped, respectively, each axial coil having first and second ends terminating at respective core first and second ends, and both first coil and core ends substantially coterminating in a first common plane transverse to the axes so that a test article can be passed in close proximity to coil and core first ends and both second coil and core ends substantially coterminating in a second common plane transverse to the coil axes, the magnetically permeable backing member attached immediately adjacent to and substantially covering the core and coil coterminal second ends of both axial coils in the second common plane.

12. The eddy current probe of claim 11 wherein said backing plate has a permeability selected so that the assembly has a low operating frequency of about 5 kHz or lower for enhanced depth of electromagnetic field penetration in a test article.

13. The eddy current probe of claim 11 wherein said backing plate is formed of a material having a permeability of about 500 or greater.

14. The eddy current probe of claim 11 further comprising a core for each coil, each of the cores having a D-shaped cross-section around which a coil is wound, the flat surfaces of the D-shaped cross-sections disposed substantially adjacent and parallel to each other.

15. An eddy current probe for non-destructive testing of alloys, comprising:

a probe housing with a longitudinal axis;

an induction enhancing member, an axial test coil member having an radial outer envelope and with first and second ends mounted in the probe housing with the coil axis in a plane transverse to the probe longitudinal axis to generate eddy currents in a test specimen of one of the alloys to be tested with the first coil end directed radially inward toward and the second coil end directed radially away from the probe longitudinal axis such that the second coil end is positionable proximate and normal to the tested alloy to generate eddy currents in the alloy, the eddy currents being generated upon excitation by an alternating current, the coil comprising a core with first and second ends around which the coil is wrapped, the coil having first and second ends terminating at corresponding core first and second ends, coil and core first ends substantially terminating in a first common plane transverse to the axes so that a test article can be passed in close proximity to coil and core first ends with coil and core second ends substantially terminating in a second common plane transverse to the coil axis; and an inductance enhancing member attached immediately adjacent to and substantially covering the core and coil second ends in the second common plane and terminating radially at the outer envelope of the coils, the inductance enhancing member having a permeability selected so that the depth of penetration of the test eddy currents is optimized for the alloys to be tested.

16. The eddy current probe of claim 15 wherein the test coil member comprises two coils disposed side by side and having parallel axes.

17. The eddy current probe of claim 15 wherein the inductance enhancing member is formed of a material having a permeability of about 500 or greater.

18. The eddy current probe of claim 15 wherein said test coil member includes at least two coils of matched inductance.

19. The eddy current probe of claim 15 further comprising a core for each coil, each of the cores having a D-shaped cross-section around which a coil is wound, the flat surfaces of the D-shaped cross-sections disposed substantially adjacent and parallel to each other.

20. The eddy current probe of claim 15 wherein the inductance enhancing member .covers the second coil end.

21. The eddy current probe of claim 15 wherein said backing plate has a permeability selected so that the assembly has a low operating frequency of about 5 kHz for enhanced depth of electromagnetic field penetration in a test alloy.

* * * * *